US007368628B2

(12) United States Patent
Kawagoe et al.

(10) Patent No.: US 7,368,628 B2
(45) Date of Patent: May 6, 2008

(54) METHODS FOR ACCUMULATING ARBITRARY PEPTIDES IN PLANT PROTEIN BODIES

(75) Inventors: Yasushi Kawagoe, Ibaraki (JP); Fumio Takaiwa, Ibaraki (JP)

(73) Assignee: National Institute of Agrobiological Sciences, Ibaraki (JP)

( * ) Notice: Subject to any disclaimer, the term of this patent is extended or adjusted under 35 U.S.C. 154(b) by 0 days.

(21) Appl. No.: 10/514,263

(22) PCT Filed: May 13, 2003

(86) PCT No.: PCT/JP03/05955

§ 371 (c)(1),
(2), (4) Date: Nov. 18, 2005

(87) PCT Pub. No.: WO03/097836

PCT Pub. Date: Nov. 27, 2003

(65) Prior Publication Data
US 2006/0090223 A1  Apr. 27, 2006

(30) Foreign Application Priority Data
May 15, 2002  (JP) .............................. 2002-139836

(51) Int. Cl.
C12N 15/62 (2006.01)
C12N 15/82 (2006.01)
(52) U.S. Cl. .................. 800/278; 435/69.1; 435/320.1; 530/300; 536/23.6; 800/285
(58) Field of Classification Search ............... 435/69.1, 435/320.1, 468; 530/370; 536/23.6; 800/278, 800/295, 320.2
See application file for complete search history.

(56) References Cited

U.S. PATENT DOCUMENTS 5,990,384 A * 11/1999 Bagga et al. ............... 800/278

FOREIGN PATENT DOCUMENTS

JP  2-79983  3/1990
JP  3 141 084  2/2001

OTHER PUBLICATIONS

Masamura et al., 1990, Mol. Gen. Genet 221:1-7.*
Shorrosh (1992) Plant Molecular Biology 18:151-154.*
Baldwin et al., "Granulocyte-macrophage colony-stimulating factor enhances neutrophil function in acquired immunodeficiency syndrome patients," *Proc. Natl. Acad. Sci. USA*, 1988, 85:2763-2766.
Choi et al., "Messenger RNA targeting of rice seed storage proteins to specific ER subdomains," *Nature*, 2000, 407:765-767.
Christou et al., "Production of Transgenic Rice (*Oryza Sativa* L.) Plants from Agronomically Important Indica and Japonica Varieties Via Electric Discharge Particle Acceleration of Exogenous DNA Into Immune Zygotic Embryos," *Bio/Technology*, 1991, 9:957-962.

Dalbadie-McFarland et al., "Oligonucleotide-directed mutagenesis as a general and powerful method for studies of protein function," *Proc. Natl. Acad.Sci. USA*, 1982, 79:6409-6413.
Datta, "Polyethylene-Glycol-Mediated Direct Gene Transfer to Indica Rice Protoplasts and Regeneration of Transgenic Plants," *Gene Transfer to Plants*, 1995, Chapter 8, pp. 66-74.
Hashimoto-Gotoh et al., "An oligodeoxyribonucleotide-directed dual amber method for site-directed mutagenesis," *Gene*, 1995, 152:271-275.
Hiei et al., "Efficient transformation of rice (*Oryza sativa* L.) mediated by *Agrobacterium* and sequence analysis of the boundaries of the T-DNA," *Plant J.*, 1994, 6(2):271-282.
Iida et al., "A rice (*Oryza sativa* L.) mutant having a low content of glutelin and a high content of prolamine," *Theor. Appl. Genet.*, 1993, 87:374-378.
Katsube et al., "Accumulation of Soybean Glycinin and Its Assembly with the Glutelins in Rice," *Plant Physiol.*, 1999, 120:1063-1073.
Kramer et al., "The gapped duplex DNA approach to oligonucleotide-directed mutation construction," *Nuc. Acids Res.*, 1984, 12(24):9441-9456.
Kramer and Fritz, "Oligonucleotide-Directed Construction of Mutations via Gapped Duplex DNA," *Methods Enzymol.*, 1987, 154:350-367.
Kunkel, "Rapid and efficient site-specific mutagenesis without phenotypic selection," *Proc. Natl. Acad. Sci. USA*, 1985, 82:488-492.
Kunkel et al., "Efficient Site-Directed Mutagenesis Using Uracil-Containing DNA," *Meth. Enzymol.*, 1991, 204:125-139.
Mark et al., "Site-specific mutagenesis of the human fibroblast interferon gene," *Proc. Natl. Acad. Sci. USA*, 1984, 81:5662-5666.
Mitsukawa et al., "Molecular Cloning and Characterization of a Cysteine-rich 16.6 kDa prolamin in rice seeds," *Biosci. Biotechnol. Biochem.*, 1999, 63(11):1851-1858.
Mitsukawa et al., "Amino Acid Sequencing and cDNA Cloning of Rice Seed Storage Proteins, the 13kDa Prolamins, Extracted from Type 1 Protein Bodies," *Plant Biotechnol.*, 1999, 16(2):103-113.
Nagel et al., "Electroporation of binary Ti plasmid vector into *Agrobacterium tumefaciens* and *Agrobacterium rhizogenes*," *FEMS Microbiol. Lett.*, 1990, 67:325-328.
Toki et al., "Expression of a Maize Ubiquitin Gene Promoter-*bar* Chimeric Gene in Transgenic Rice Plants," *Plant Physiol.*, 1992, 100:1503-1507.

(Continued)

*Primary Examiner*—Anne Marie Grunberg
*Assistant Examiner*—Brendan O. Baggot
(74) *Attorney, Agent, or Firm*—Fish & Richardson P.C.

(57) ABSTRACT

The present inventors presumed that rice globulins accumulating in vacuole-derived type II protein bodies comprise a vacuolar translocating signal and proceeded to identify such a signal. As a result, fusion proteins composed of a 15 amino acid residue peptide of globulin, extending from the 72nd leucine residue to the 86th serine residue, added to the C terminus of GFP were surprisingly found to be intracellularly localized to non-vacuole-derived type I protein bodies (PB-I), and not to vacuole-derived type II protein bodies (PB-II). Furthermore, based on this 15 amino acid residue sequence, the consensus sequence "QCCXQ" (where X is an arbitrary amino acid), which is conserved in plants, was discovered. Accordingly, the present invention suggests that arbitrary peptides can be accumulated in plant endosperm tissues by adding the QCCXQ sequence thereto.

2 Claims, 4 Drawing Sheets

OTHER PUBLICATIONS

Nakamura et al., "Comparative Bio-antimutagenicity of Common Vegetables and Traditional Vegetables in Kyoto," *Biosci. Biotechnol. Biochem.*, 1998, 62(6):1161-1165.

Tanaka et al., "The Relationship of the Feces Protein Particles to Rice Protein Bodies," *Agr. Biol. Chem.*, 1975, 39(2):515-518.

Wang et al., "Site-Specific Mutagenesis of the Human Interleukin-2 Gene: Structure-Function Analysis of the Cysteine Residues," *Science*, 1984, 224:1431-1433.

Zheng et al., "The Bean Seed Storage Protein β-Phaseolin Is Synthesized, Processed, and Accumulated in the Vacuolar Type-II Protein Bodies of Transgenic Rice Endosperm," *Plant Physiol.*, 1995, 109:777-786.

Zoller and Smith, "Oligonucleotide-directed mutagenesis using M13-derived vectors: an efficient and general procedure for the production of point mutations in any fragment of DNA," *Nucl. Acids Res.*, 1982, 10(20):6487-6500.

Zoller and Smith, "Oligonucleotide-Directed Mutagenesis of DNA Fragments Cloned into M13 Vectors," *Methods Enzymol.*, 1983, 100:468-500.

Kawagoe et al., "The critical role of disulfide bond formation in protein sorting in the endosperm of rice," *The Plant Cell*, 17:1141-1153, 2005.

Masumura, *Annual Report of the Iijima Memorial Foundation for the Promotion of Food Science and Technology*, 1997, 1995: 178-81 (w/English translation).

Tanaka, *Plant Tissue Culture Symposium*, 1994, 4:47-50, Abstract (w/English translation).

* cited by examiner

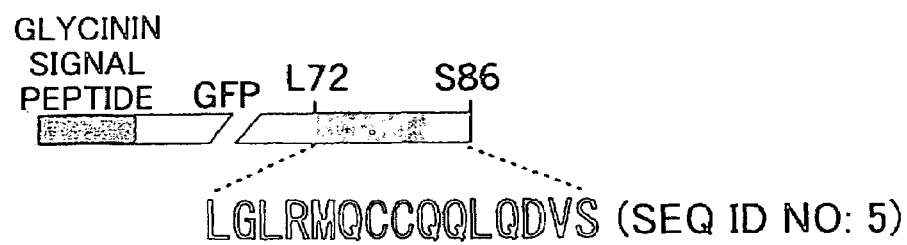
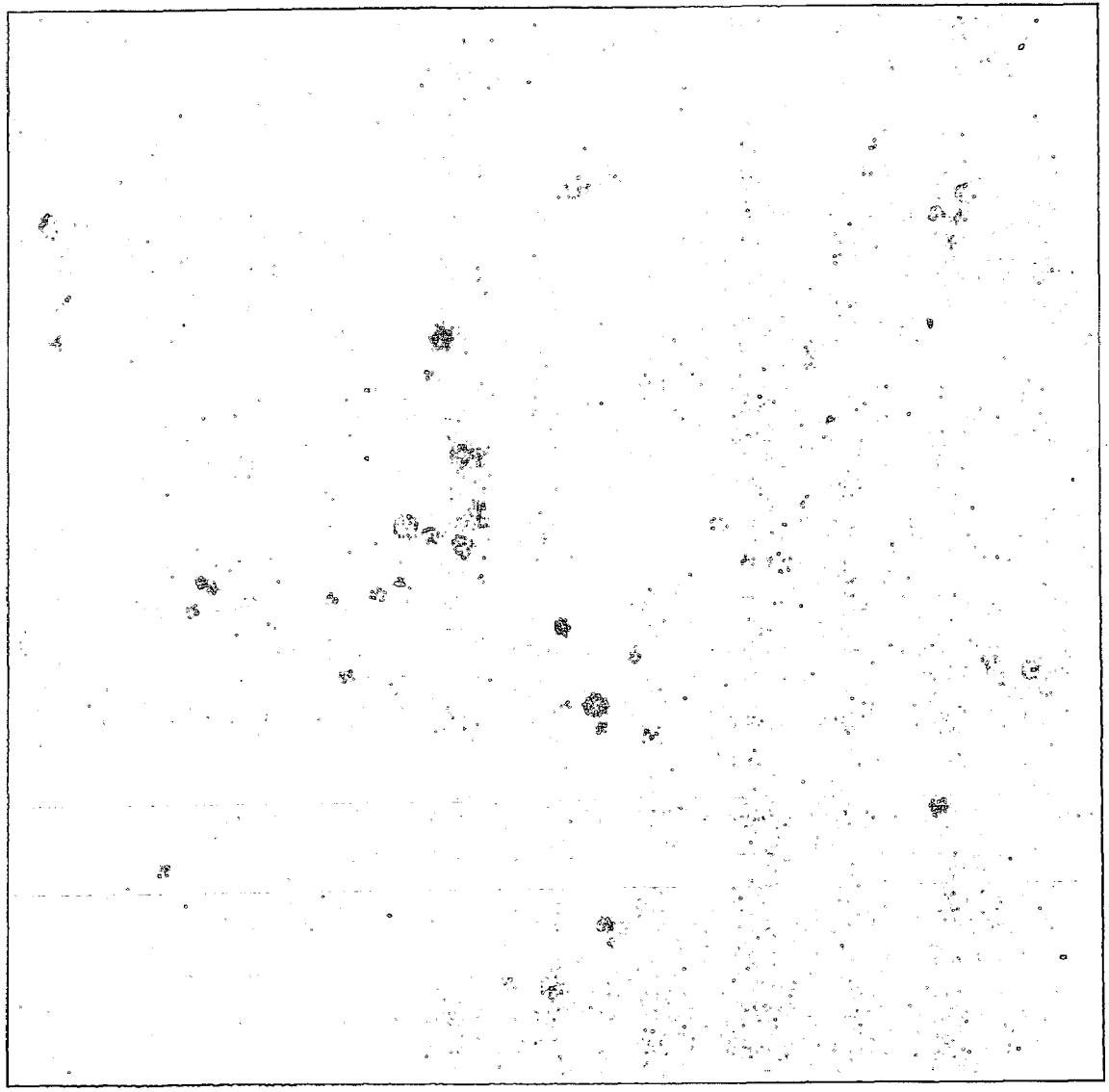
FIG. 2

| | | |
|---|---|---|
| RICE GLOBULIN | LGLRMQCCQQLQDVS 86 | (SEQ ID NO: 5) |
| RICE 16.6-kDa PROLAMINE (λRP16) | QVMRQCCQQMRLMA 83 | (SEQ ID NO: 8) |
| RICE 13-kDa PROLAMINE (pProl17) | QVMQQCCQQLRMIA 82 | (SEQ ID NO: 9) |
| RICE 13-kDa PROLAMINE (λRM7) | QVMQQCCQQLRLVA 88 | (SEQ ID NO: 10) |
| RICE 10-kDa PROLAMINE (λRP10) | ALLQQCCMQLQGMM 80 | (SEQ ID NO: 11) |
| CORN 15-kDa ZEIN (cZ15A3) | QPLRQCCQQMRMM 95 | (SEQ ID NO: 12) |
| OAT AVENIN | HVMRRQCCRQLAQIP 90 | (SEQ ID NO: 13) |
| | * * * * * | |
| CONSENSUS SEQUENCE (1) | QCCQQ / M / R | (SEQ ID NO: 2) |
| CONSENSUS SEQUENCE (2) | LRMQCCQQLQXV / MQQ M MR M / R R QM I / A | (SEQ ID NO: 3) |

FIG. 3

METHODS FOR ACCUMULATING ARBITRARY PEPTIDES IN PLANT PROTEIN BODIES

TECHNICAL FIELD

The present invention relates to methods for accumulating arbitrary peptides in plant endosperm tissues.

BACKGROUND ART

Findings to date suggest three types of methods for expressing and accumulating high levels of exogenous gene products in rice endosperm tissues while avoiding degradation during the ripening process. In the first of these methods that are now actually in use, the desired protein or peptide is introduced into the variable region of a seed storage protein of rice, or some other species, for translocation into vacuole-derived type II protein bodies (PB-IIs) as a part of that storage protein. The second method is useful in cases where the desired protein does not originally comprise a vacuolar translocation signal. It involves attaching a signal peptide to the N terminus of the desired protein and secreting it to the cell wall apoplast. In the third method, a signal peptide is attached to the N terminus of the desired protein and a known endoplasmic reticulum localization signal, such as KDEL (SEQ ID NO: 17) or HDEL (SEQ ID NO: 18), is attached to the C terminus; the desired protein is then accumulated in the endoplasmic-reticulum.

Rice endosperm comprises PB-Is, protein bodies which are not vacuole-derived and in which primarily prolamines accumulate. Since PB-Is are produced directly from the endoplasmic reticulum, their production process is vastly different from that of vacuole-derived PB-II protein bodies. With regards to the accumulation of prolamines in PB-Is, a Washington State University group reported that prolamine mRNAs are transported to PB-Is via their 3' untranslated region and translated therein into prolamines (Choi et al. Nature 2000, 407: 765-767).

DISCLOSURE OF THE INVENTION

The present invention was made under the above circumstances. An objective of the present invention is to provide DNAs that encode peptides having the activity of accumulating in type I protein bodies in plant endosperm tissues, and methods for using the same. Specifically, the present invention aims to provide methods for accumulating arbitrary peptides in plant endosperm tissues. In addition, the present invention aims to provide kits for such methods.

The present inventors presumed that rice globulins accumulating in vacuole-derived type II protein bodies (PB-IIs) comprise vacuolar translocation signals and proceeded to identify these signals. Specifically, the signal peptide of glycinin $A_{1a}B_{1b}$, which is a soy bean seed storage protein, was added to the N terminus of GFP, and a full-length globulin lacking the signal peptide, or a part of the same, was added to the C terminus of GFP. A globulin promoter was used as a promoter for gene expression. Using an Agrobacterium-mediated method, a callus derived from rice seed was infected to produce transformants. Intracellular localization of the fusion protein to endosperm tissues was observed using a confocal laser scanning microscope.

As a result, the fusion proteins, which had a sequence consisting of the 21st glycine residue (G21) to the 111 st glutamine residue (Q111) of globulin added to the C terminus of GFP, surprisingly did not show intracellular localization to vacuole-derived type II protein bodies (PB-IIs), but rather localized to type I protein bodies (PB-Is), which are not vacuole-derived. In addition, the sequence from G21 to Q111 was split into two fragments, one extending from G21 to R59 and the other from R68 to Q111. In the same way as above, transformants having one or the other of the two sequences added to the C terminus of GFP were produced, and their intracellular localizations were observed. The results indicated that fusion proteins having the R68 to Q111 sequence added to the C terminus of GFP, localized to type I protein bodies (PB-Is). The sequence from R68 to Q111 was again divided. Resulting sequences, one extending from L72 to S86 and the other from A92 to S104, were added to the C terminus of GFP, respectively. Transformants comprising one or the other of these constructs were produced, and intracellular localizations were observed, as above. As a result, the fusion proteins, which had a 15 amino acid residue peptide extending from L72 to S86 added to the C terminus of GFP, localized to type I protein bodies (PB-Is).

This 15 amino acid sequence was identified to be highly homologous to a conserved region in the rice prolamine gene family (Matsukawa et al. Biosci. Biotechnol. Biochem. 1999, 63, 1851-1858). In particular, the two consecutive residues, and the glutamine residues upstream and downstream of the cysteine residues (QCCQQ) (SEQ ID NO: 14) are conserved in the 16.6-kDa prolamine (λRP16) and 13-kDa prolamine (pProl17, λRM7). In the 10-kDa prolamine (λRP10), the glutamine is replaced with a methionine, resulting in the QCCMQ sequence (SEQ ID NO: 15). Similar sequences, QCCQQ (SEQ ID NO: 14) and QCCRQ (SEQ ID NO: 16), exist in a corn seed storage protein, the 15-kDa zein, and an oat seed storage protein, avenin, respectively. Accordingly, QCCXQ (SEQ ID NO: 1) (wherein X is an arbitrary amino acid) was found to be a consensus sequence for these sequences. These observations show that an arbitrary peptide can be accumulated in plant endosperm tissues by adding this conserved, consensus sequence "QCCXQ" (SEQ ID NO: 1) to the arbitrary peptide.

Thus, the present invention relates to methods for accumulating arbitrary peptides in plant endosperm tissues, and specifically provides as follows.

[1] A method for accumulating an arbitrary peptide in the endosperm tissue of a plant, which comprises the steps of:
(a) introducing a vector comprising a DNA encoding a fusion peptide arising by fusing an arbitrary peptide with a peptide comprising at least the amino acid sequence of any one of SEQ ID NOs: 1 to 3 and having the activity of accumulating in a type I protein body in a plant endosperm tissue; and
(b) regenerating the plant cell into a plant.

[2] The method of [1], wherein the plant is a rice plant.

[3] A DNA encoding a peptide comprising at least the amino acid sequence of any one of SEQ ID NOs: 1 to 3 and having the activity of accumulating in a type I protein body in a plant endosperm tissue.

[4] The DNA of [3], wherein the plant is a rice plant.

[5] A DNA encoding a fusion peptide arising by fusing an arbitrary protein with a peptide comprising at least the amino acid sequence of any one of SEQ ID NOs: 1 to 3 and having the activity of accumulating in a type I protein body in a plant endosperm tissue and.

[6] The DNA of [5], wherein the plant is a rice plant.

[7] A vector comprising the DNA of any one of [3] to [6].

[8] A transformed plant cell, into which a vector comprising the DNA of [5] or [6] is inserted.

[9] A transformed plant, which comprises the transformed plant cell of [8].

[10] A transformed plant, which is an offspring or clone of the transformed plant of [9].

[11] A reproductive material of the transformed plant of [9] or [10].

[12] A kit for performing the method of [1], which comprises any one of the following (a) to (c):

(a) a DNA encoding a fusion protein arising by a fusion of an arbitrary peptide with a peptide comprising at least the amino acid sequence of any one of SEQ ID NOs: 1 to 3 and having the activity of accumulating in a type I protein body in a plant endosperm tissue;

(b) a DNA encoding the peptide of (i); and (c) a vector comprising the DNA of (a) or (b).

[13] The kit of [12], wherein the plant is a rice plant.

In the present invention, the term "peptide" refers to a compound in which amino acids are linked by peptide bonds. Thus, in the context of the present invention, longer peptides such as "polypeptides" and "proteins" are also encompassed by the term "peptide".

In the present invention, the term "protein body" refers to an organelle surrounded by a lipid bilayer membrane that is found in storage tissues of seeds and such, and primarily accumulates storage proteins therein. Two types of protein bodies produced from different origins exist in rice endosperm. Protein bodies (PB-IIs) in which storage proteins such as glutelins and globulins are accumulated are produced from vacuoles, whereas protein bodies (PB-Is) in which storage proteins such as prolamine accumulate are produced directly from the endoplasmic reticulum. Whilst PB-IIs take various forms, PB-Is are spherical granules.

Unless otherwise specified, "DNA" in the present invention can take any form, and comprises genomic DNA, cDNA, and chemically synthesized DNA.

The present invention provides methods for accumulating arbitrary peptides in plant endosperm tissues. The methods of the present invention comprise the steps of: (a) introducing a vector comprising a DNA encoding a fusion peptide of (i) a peptide comprising at least the amino acid sequence "QCCXQ" (SEQ ID NO: 1) and having the activity of accumulating in a type I protein body in a plant endosperm tissue and (ii) an arbitrary peptide; and (b) regenerating the plant cell into a plant.

In the present invention, so long as the above-mentioned peptide (i) comprises at least the amino acid sequence "QCCXQ" (SEQ ID NO: 1) and has the activity of accumulating in type I protein bodies in plant endosperm tissues, it is not limited to an amino acid sequence other than the amino acid sequence "QCCXQ" (SEQ ID NO: 1). The peptide preferably comprises the amino acid sequence "QCC(Q/M/R)Q" (SEQ ID NO: 2), more preferably the amino acid sequence "(L/M)(R/Q)(M/Q/R)QCC(Q/M/R)Q (L/M/Q)(Q/R/M/A)X(V/M/I)" (SEQ ID NO: 3), still more preferably the amino acid sequence "LRMQCCQQLQDV" (SEQ ID NO: 4), and even more preferably the amino acid sequence "LGLRMQCCQQLQDVS" (SEQ ID NO: 5). Herein, (L/M), (R/Q), (M/Q/R), (Q,M,R), (L/M/Q), (Q/R/M/A), and (V/M/I) mean that any one of the shown amino acids may be used.

The peptides of the present invention can be naturally-occurring proteins or a part thereof, or can also be modified peptides derived from these naturally-occurring proteins. For modification of amino acids while maintaining the basic activities of the peptide, it is preferable to exchange the amino acids for other amino acids having similar side-chain characteristics. Examples of properties of amino acid side chains include: hydrophobic amino acids (A, I, L, M, F, P, W, Y, V), hydrophilic amino acids (R, D, N, C, E, Q, G, H, K, S, T), and amino acids comprising the following side chains: aliphatic side-chains (G, A, V, L, I, P); hydroxyl group-containing side-chains (S, T, Y); sulfur atom-containing side-chains (C, M); carboxylic acid- and amide-containing side-chains (D, N, E, Q); base-containing side-chain (R, K, H); and aromatic-containing side-chains (H, F, Y, W) (The letters within parentheses indicate the one-letter amino acid codes). It is well known that an amino acid sequence having a deletion, addition, and/or substitution of one or more amino acid residues in the sequence can retain the original biological activity (Mark, D. F. et al. Proc. Natl. Acad. Sci. U.S.A. 81:5662-5666 (1984); Zoller, M. J. and Smith, M. Nucleic Acids Res. 10:6487-6500 (1982); Wang, A. et al. Science 224:1431-1433; Dalbadie-McFarland, G. et al. Proc. Natl. Acad. Sci. U.S.A. 79:6409-6413 (1982)).

Site-directed mutagenesis is an example of a method for altering amino acid sequences (Hashimoto-Gotoh, T. et al. (1995) Gene 152, 271-275; Zoller, M J, and Smith, M. (1983) Methods Enzymol. 100, 468-500; Kramer, W. et al. (1984) Nucleic Acids Res. 12, 9441-9456; Kramer W, and Fritz H J (1987) Methods. Enzymol. 154, 350-367; Kunkel, T A (1985) Proc Natl Acad Sci USA. 82, 488-492; Kunkel (1988) Methods Enzymol. 85, 2763-2766).

The peptides produced as described can be assayed for the activity of accumulating in type I protein bodies in plant endosperm tissues, as in the Example, by using a microscope to observe the intracellular localization of a fusion protein formed by fusing a label protein such as GFP with the target amino acid sequence. In addition, if the label protein is a fluorescent protein such as GFP, the activity level can be measured by fluorescence intensity.

In the context of the present invention, the above-mentioned peptide (ii) is not particularly limited. A desired protein that one wishes to accumulate in type I protein bodies in plant endosperm tissues can be used in the present invention. Examples of such peptides include highly valuable peptides, such as peptides comprising highly nutritious amino acid compositions, peptides functioning physiologically in humans or livestock, edible vaccines, antibodies, enzyme proteins, and such. In addition to these peptides, peptides that can be expected to change the physical properties of protein bodies (PB-Is) by targeting PB-Is can also be examples, even if the peptides themselves are not highly valuable. Thus, accumulation of peptides other than prolamines in PB-Is can be expected to affect interactions among the prolamine proteins in PB-Is, resulting in inhibition of crystallization. Examples of peptides comprising this kind of characteristic include peptides with a high water-holding capacity, peptides comprising a large number of hydrophilic amino acid residues, and such.

In the present invention, DNAs encoding fusion peptides made by fusing peptides (i) and (ii) can be prepared by binding DNAs encoding peptide (i) and DNAs encoding peptide (ii). In addition, DNAs encoding the fusion peptides can be bound to DNAs encoding signal peptides. Examples of signal peptides are not particular limited and include soybean seed storage protein and glycinin $A_{1a}B_{1b}$.

These fusion peptide DNAs can be prepared using PCR and such, from genomic DNA or mRNA derived from organisms (preferably plants), or can be chemically synthesized. The binding of these DNAs can be achieved using conventional genetic engineering methods. These DNAs can be bound in any manner. For example, DNAs encoding peptide (i) and peptide (ii) can be bound such that peptide (i) is added to the C terminus of peptide (ii). In addition, the DNAs encoding each of the peptides can be bound such that a signal peptide is added to the N terminus of peptide (ii).

A DNA sequence encoding peptide (i) of the present invention can be determined from the amino acid sequence of the above-mentioned peptide, in accordance with the codon table. In such cases, codons suitable for rice endosperm tissues can be used; however, there is no limitation. Furthermore, a globulin DNA sequence can also be used as a DNA sequence encoding peptide (i). Once a DNA sequence encoding peptide (i) has been determined, the DNA can be synthesized using methods well-known in the art. DNAs encoding signal peptides can also be synthesized in the same way.

The binding of DNAs encoding peptides (i) and DNAs encoding peptides (ii) (or otherwise, the synthesis of DNAs encoding fusion peptides of peptides (i) and (ii)) can be carried out, for example, by PCR using primers comprising DNA sequences encoding peptides (i). DNAs encoding signal peptides can be bound with DNAs encoding the peptides (ii) using similar methods.

According to the present invention, vectors comprising a DNA encoding the above-described fusion proteins can be introduced into plant cells by one skilled in the art using known methods such as the agrobacterium method, electroporation method, and the particle gun method.

For the agrobacterium method as described above, ultra-high-speed transformation of monocots (JP Patent No. 3141084), for example, can be used. In addition, the method of Nagel et al. and such can be used (Microbiol. Lett., 1990, 67, 325). According to this method, agrobacterium is transformed by a recombinant vector and introduced to plant cells using a known method, such as the leaf disc method. The above vectors comprise, for example, a promoter to express a DNA encoding the above-described fusion protein in a plant subsequent to introduction into that plant. Generally, a DNA encoding the above-described fusion protein is placed downstream of such a promoter and, moreover, a terminator sequence is placed downstream of the DNA. A recombinant vector used for this purpose may be suitably determined by one skilled in the art, depending on the transfection method or type of plant. The above-mentioned promoter may be, for example, a rice globulin promoter, a cauliflower mosaic virus derived CaMV35S promoter, or an ubiquitin promoter from maize (Unexamined Published Japanese Patent Application No. (JP-A) Hei 2-79983).

The above-mentioned terminator may be, for example, a cauliflower mosaic virus-derived terminator or nopalin synthase terminator. However, so long as they function as a promoter or terminator in a plant of interest, there are no particular limitations thereon.

Examples of plant cells to which a vector comprising a DNA that encodes the above-mentioned fusion peptide may be introduced include plant cells derived from gramineous plants comprising rice, corn, oats, wheat, barley, and such; however, the present invention is not limited to these. Furthermore, any plant cell form can be used, such as plant cells, calluses, suspension cultured cells, and explants from leaves, roots, stems, flowers, and blastodiscs within seeds.

In order to efficiently select transformed plant cells introduced with a vector comprising a DNA encoding the above-described fusion protein, the above recombinant vector preferably harbors an appropriate selective marker gene, or is introduced into plant cells together with a plasmid vector harboring a selective marker gene. Selective marker genes used for this purpose include, for example, the hygromycin phosphotransferase gene, which confers resistance to the antibiotic hygromycin; the neomycin phosphotransferase gene, which confers resistance to kanamycin or gentamycin; and the acetyltransferase gene, which confers resistance to the herbicide, phosphinothricin.

Plant cells transfected with a recombinant vector are plated and cultured on a known selective medium containing an appropriate selective drug, depending on the type of the introduced selective marker gene. In this way, one can obtain transformed plant cultured cells.

Regeneration of a plant can be carried out by methods known to those skilled in the art depending on the plant cell type (Toki et al., Plant Physiol., 1995, 100, 1503-1507). Several techniques have already been established to generate transformed rice plants, and those techniques are widely used in the field of the present invention. For example, rice plants can be regenerated after introducing a DNA using (1) polyethylene glycol (suitable for Indica rice varieties) (Datta, S. K. et al., In Gene Transfer To Plants (Potrykus I and Spangenberg Eds.), 1995, 66-74); (2) electric pulse (suitable for Japonica rice varieties) (Toki et al., Plant Physiol., 1992, 100, 1503-1507); (3) particle gun method (Christou et al., Bio/technology, 1991, 9, 957-962); or (4) agrobacteria (Hiei et al., Plant J., 1994, 6, 271-282). In the present invention, any of these methods can preferably be used.

The plants regenerated from transformed plant cells are subsequently cultured in an acclimatization medium. After the acclimatized regenerated plants are grown under normal cultivation conditions, plants can be obtained. Seeds can also be obtained when these plants mature and produce fruit.

The exogenously introduced DNA or nucleic acid in a thus regenerated and grown transformed plant can be confirmed by known methods, such as PCR or Southern hybridization, or by analyzing the nucleotide sequence of the plant's nucleic acid. To extract DNA or nucleic acid from a transformed plant, the known method of J. Sambrook et al. may be used (Molecular Cloning, $2^{nd}$ edition, Cold Spring Harbor laboratory Press, 1989).

To conduct PCR analysis of the DNA encoding the above-described fusion protein, which exists in the regenerated plant body, an amplification reaction is carried out using the nucleic acid that extracted from the regenerated plant by the above-mentioned method as a template. When the nucleic acid is a DNA, the amplification reaction may be carried out in a reaction mixture containing, as primers, synthesized oligonucleotides comprising nucleotide sequences appropriately selected according to the DNA's nucleotide sequence. An amplified DNA fragment comprising a DNA encoding the above-described fusion protein may be obtained by repeating the denaturation, annealing, and extension steps for DNA several dozen cycles of the amplification reaction. The respective amplified DNA fragments can be separated by, for example, electrophoresing the reaction solution containing the amplified products on agarose gel. DNA fragments corresponding to a DNA encoding the above-described fusion protein can then be confirmed.

Having obtained a transformed plant in which a DNA encoding the above-described fusion protein has been inserted into the chromosomes, one can obtain the plant's offspring by sexual or non-sexual reproduction. Also, it is possible to mass-produce such plants by obtaining reproductive materials (such as seeds, fruits, cuttings, stem tubers, root tubers, shoots, calluses, and protoplasts) from the above plant, or its offspring or clones.

In addition, the accumulation of the arbitrary peptide in endosperm tissues of the transformed plants can be confirmed by: (1) extracting total protein from the seeds of transformed and non-transformed plants, respectively; (2)

separating the proteins using SDS-polyacrylamide gel electrophoresis; and then (3) comparing the two. In addition, by using antibodies against the target peptides, quantitative analysis can also be carried out by Western blotting, ELISA, and such. For example, the accumulation and its amount can be confirmed using the following method.

First, fully mature seeds are physically ground finely. Wooden mallets and such can be used for seed grinding, and specialized equipment can also be used when dealing with large quantities of seeds. The ground seed powder is then added to the protein extraction buffer of Example 2 and mixed. All of the protein is solubilized by allowing the mixture to stand half a day at room temperature. To confirm whether proteins comprising the target protein are comprised in the extracted proteins, antibodies against peptides (i) or (ii) of the present invention can be used. For example, anti-globulin antibodies can be used in Western blotting, ELISA, and such to detect and quantify the proteins. As one example in the present invention, a Western blotting method using anti-GFP antibodies is used to detect and quantify proteins comprising the peptide of SEQ ID NO: 5 (FIG. 4).

In addition, the present invention provides useful kits for carrying out the methods of the present invention. These kits can comprise, for example, (1) DNAs encoding the above-mentioned fusion peptides; (2) DNAs encoding the peptides (i); and (3) vectors comprising the DNAs of (1) or (2). Examples of other components that can be included in the kits of the present invention include genomic DNA libraries, cDNA libraries, vectors, plant cells, and various reagents.

Rice globulins (α globulins) comprise a signal peptide at their N terminus. The regions from glycine 21 to glutamine 111 and from glutamine 148 to the stop codon are conserved regions with high homology to the wheat seed storage protein, glutenin. The region between these two conserved regions is referred to as a variable region since it has low homology to wheat glutenin.

FIG. 2 shows a fusion protein composed of the 15 amino acid residues (L72-S86) added to the C terminus of GFP, and a photograph depicting intracellular localization of this fusion protein.

FIG. 3 shows amino acid sequences with high homology to the 15 amino acid residue peptide that are necessary for globulins to be transported to PB-Is. Since rice prolamines are members of a comparatively large multi-gene family, the genes shown in the figure are one portion of prolamine genes. One characteristic of prolamine genes is that they comprise a sequence shown as a consensus sequence, or sequences similar to the same. Corn 15-kDa zein and oat avenin also comprise similar amino acid sequences.

Figure 4:
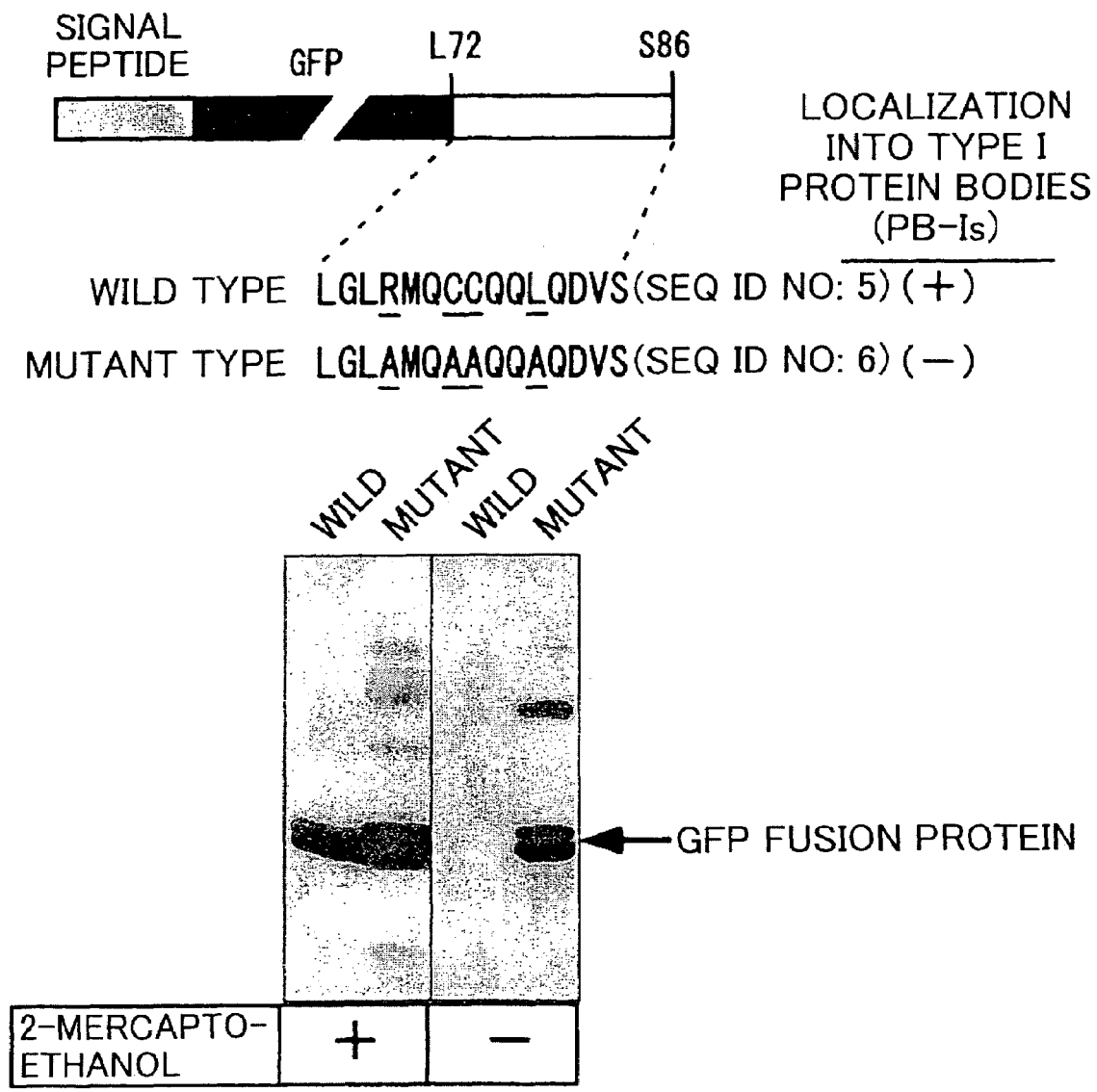

FIG. 4 shows fusion proteins with the wild type or mutant type 15 amino acid residues added to the C terminus of GFP, and a photograph showing the results of solubilization analysis for each of these GFP fusion proteins. Total protein was extracted from fully mature seeds using a buffer with or without 5% 2-mercaptoethanol (reductant). After separating the extracted proteins using the ordinary SDS-PAGE method, anti-GFP antibodies were used to analyze the solubilization of the GFP fusion proteins (wild and mutant types) in each of the extraction buffers. In the extraction buffer with reductant, both the wild type and mutant type fusion proteins could be solubilized; however, the wild type GFP fusion protein was not solubilized in the extraction buffer without reductant.

BEST MODE FOR CARRYING OUT THE INVENTION

Herein below, the present invention is specifically described with reference to Examples; however, it is not to be construed as being limited thereto.

EXAMPLE 1

Rice seed storage proteins, globulins, accumulate in vacuole-derived type II protein bodies (PB-IIs). This suggests that globulins comprise a vacuolar translocation signal in a specific site in the protein. The present inventors began research that focused on identifying vacuolar translocation signals of globulin. GFP protein sGFPs (S65Ts) were used as reporter proteins. The signal peptide of glycinin $A_{1a}B_{1b}$, which is a soy bean seed storage protein, was added to the N terminus of GFP, and a full-length globulin lacking the signal peptide, or a part of the same, was added to the C terminus of GFP. A globulin promoter was used as a promoter for gene expression. Using an Agrobacterium-mediated method (ultrahigh-speed transformation of monocots (JP Patent No. 3141084)), a callus derived from rice seed was infected to produce transformants. Intracellular localization of the fusion protein in endosperm tissues was observed using a confocal laser scanning microscope. Surprisingly, when a globulin fragment extending from the 21st glycine residue (G21) to the 111st glutamine residue (Q111) was added to the C terminus of the GFP, intracellular localization of fusion proteins was observed not in vacuole-derived type II protein bodies (PB-IIs), but rather in type I protein bodies (PB-Is), which are not derived from vacuoles. Thus, intracellular localization of the above-mentioned GFP fusion proteins was mostly observed in a large number of spherical granules that were 0.5 to 2.3 microns in diameter, which are presumed to be type I protein bodies (PB-Is).

Figure 1:
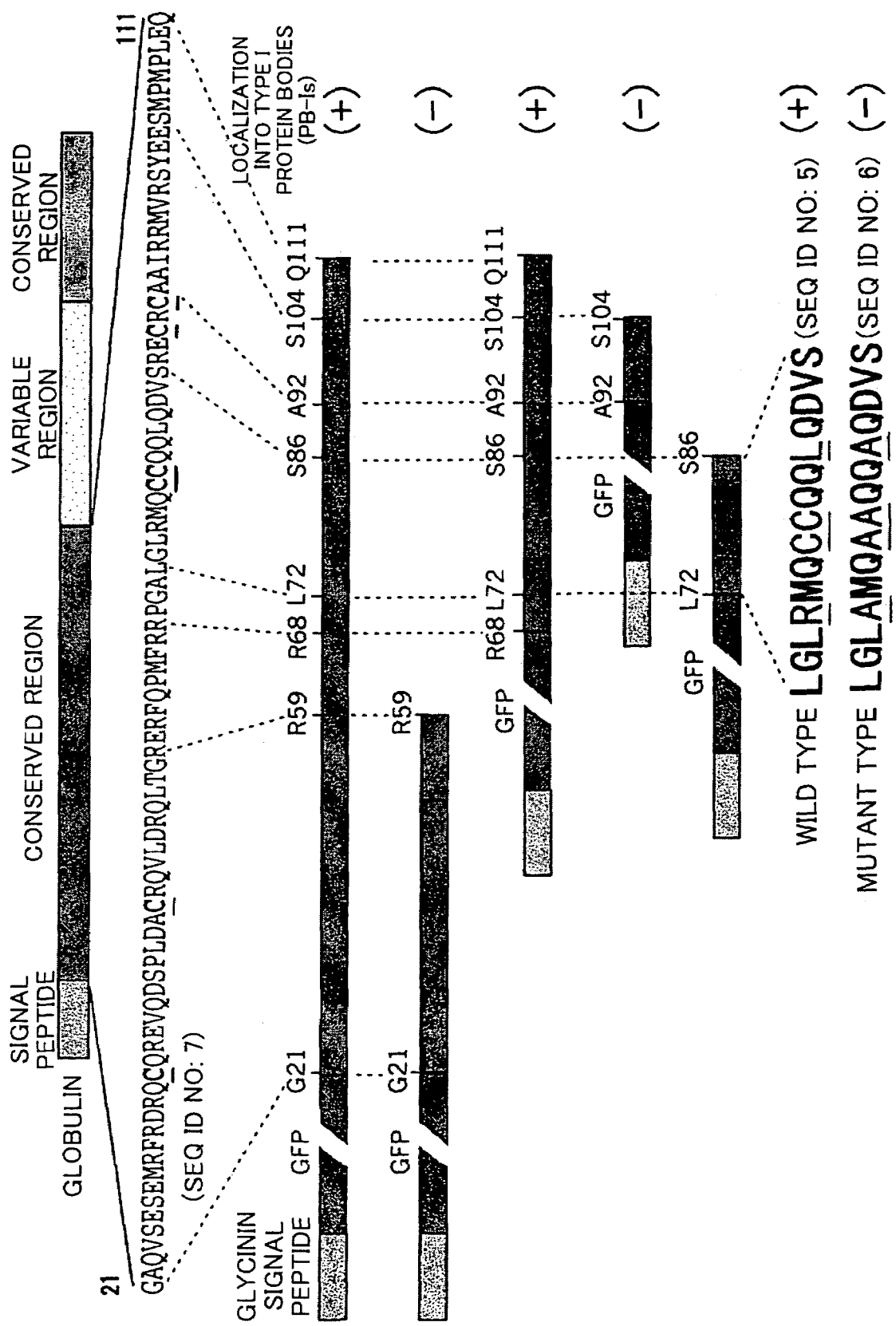
FIG. 1 shows the amino acid sequence of the conserved region of rice globulin, from glycine 21 to glutamine 111, and also shows the six GFP fusion proteins used in experiments. Intracellular localization of the fusion proteins with, from the top, the amino acid sequences of (G21-Q111), (G21-R59), (R68-Q111), (A92-S104), and (L72-S86), each added to the C terminus of GFP, was analyzed. Furthermore, intracellular localization of further fusion proteins with mutated 15 amino acid sequences added to the C terminus of GFP was analyzed. Whether or not these fusion proteins accumulated in protein bodies (PB-Is) is shown on the right with (+) or (−).

The present inventors began identification of regions essential for the above-mentioned GFP fusion proteins to accumulate in type I protein bodies (PB-Is). First, the sequence from G21 to Q111 was split into two sequences: a first extending from G21 to R59 and a second from R68 to Q111. In the same way as above, transformants with one of the two sequences added to the C terminus of GFP respectively, were produced, and intracellular localization was observed. These results indicated that fusion proteins composed of the sequence extending R68 to Q111 added to the C terminus of GFP were localized to type I protein bodies (PB-Is). To further specify the essential region, the sequence from R68 to Q111 was again divided. Resulting sequences, one from L72 to S86 and another from A92 to S104, were added to the C terminus of GFP, respectively. Transformants comprising one of these constructs were produced, and intracellular localizations was observed, as above. As a result, fusion proteins composed of the 15 amino acid residue peptide extending from L72 to S86 added to the C terminus of GFP were found to localize in type I protein bodies (PB-Is) (FIGS. 1 and 2).

Based on the tertiary structure information of a homologous protein SFA-8, a sunflower 2S albumin, it appears that the two consecutive cysteine residues at 78 and 79 positions of this 15 amino acid sequence (LGLRMQCCQQLQDVS) (SEQ ID NO: 5) forms disulfide bonds with two other cysteine residues within the globulin molecule. Thus, the GFP fusion proteins were inferred to be localized to type I protein bodies (PB-Is) because the two cysteine residues at 78 and 79 positions form disulphide bonds with other proteins in the endoplasmic reticulum lumen. To verify this hypothesis, the 15 amino acid residue peptide (LGLAMQAAQQAQDVS) (SEQ ID NO: 6), in which four residues comprising C78 and C79 (R75, C78, C79 and L82) were replaced with alanines, were added to the C terminus of GFP. As above, transformants comprising this construct were produced, and intracellular localization was observed. In this case it was found that GFP was not localized to type I protein bodies (PB-Is). In addition, in this Example, it was found that localization in type I protein bodies (PB-Is) was not caused by only the presence of cysteine residues. For example, two cysteine residues, C36 and C48, exist in the amino acid sequence from G21 to R59. However, the GFP fusion protein composed of the sequence from G21 to R59 added to the C terminus of GFP as above, is not localized to type I protein bodies (PB-Is) (FIG. 1). This suggests that the presence of cysteine residues in the amino acid to be added is necessary, but not sufficient for accumulating a desired protein in type I protein bodies (PB-Is). That is, the amino acid sequences upstream and downstream of the cysteine residues are also important.

Furthermore, the the 15 amino acid sequence (LGLRMQCCQQLQDVS) (SEQ ID NO: 5) was identified to be highly homologous to a conserved region in the rice prolamine gene family (Matsukawa et al. Biosci. Biotechnol. Biochem. 1999, 63, 1851-1858). In particular, the two consecutive cysteine residues, and the glutamine residues upstream and downstream of the cysteine residues (QCCQQ) (SEQ ID NO: 14) are conserved in the 16.6-kDa prolamine (λRP16) and 13-kDa prolamine (pProl17, λRM7). In the 10-kDa prolamine (λRP10), the glutamine is replaced with a methionine, resulting in the QCCMQ sequence (SEQ ID NO: 15). Similar sequences, QCCQQ (SEQ ID NO: 14) and QCCRQ (SEQ ID NO: 16), exist in corn seed storage protein, 15-kDa zein, and oat seed storage protein, avenin, respectively. QCCXQ (SEQ ID NO: 1) (wherein X is an arbitrary amino acid) was found to be a consensus sequence for these sequences (FIG. 3). This conserved consensus sequence appears to be essential for the accumulation of globulin in type I protein bodies (PB-Is).

In addition, considering that the above-mentioned proteins are all seed storage proteins, genes of these proteins can be surmised to be included in a gene group having the same evolutionary origin. Furthermore, since prolamines, zeins, and avenins are transported to and accumulated in protein bodies (corresponding to rice PB-Is) derived from the endoplasmic reticulum, it is presumed that the above-mentioned consensus sequence plays an essential role in the transport and accumulation of these proteins as well.

EXAMPLE 2

The present inventors found that the consecutive cysteine residues in the consensus sequence form disulfide bonds with other proteins (FIG. 4). GFP fusion proteins to which the 15 amino acid residues of wild type sequence (SEQ ID NO: 5) or mutant type sequence (SEQ ID NO: 6) are added, can be solubilized from fully mature seeds using a conventional protein extraction buffer (50 mM Tris-HCl, pH6.8, 8 M urea, 4% SDS, 20% glycerol, and 5% 2-mercaptoethanol) (Iida, S., Amano, E. and Nishio, T. 1993. Theor. Appl. Genet. 87, 374-378). However, when this extraction buffer, minus the reductant 2-mercaptoethanol, is used, proteins to which the wild-type 15 amino acid residues were added could not be solubilized. On the other hand, the GFP fusion protein to which the mutant-type 15 amino acid residues were added was easily solubilized, even in the extraction buffer without reductant. These results demonstrate that since the two cysteine residues in the consensus sequence are crosslinked to other proteins by disulfide bonds, they cannot be solubilized in buffers without reductants. In association with this finding, the addition of a reductant to the protein extraction buffer was established to be essential for the solubilization of prolamines that comprise cysteine residues (Mitsukawa et al., Biosci. Biotechnol. Biochem. 1999, 63, 1851-1858).

In summary, (1) the wild-type 15 amino acid residues have high homology with prolamine amino acid sequences; (2) GFP fusion proteins to which the wild-type 15 amino acid residues are added are localized to PB-Is; (3) most of the proteins comprised in PB-Is are prolamines; and (4) GFP fusion proteins to which the wild-type 15 amino acid residues are added are cross-linked to other proteins by disulfide bonds. On considering these facts, it can be inferred that GFP fusion proteins comprising the consensus sequence are transported to and accumulated in PB-Is because the consecutive cysteine residues in the consensus sequences form disulfide bonds with prolamines.

INDUSTRIAL APPLICABILITY

Two different types of protein bodies, PB-Is and PB-IIs, exist in rice endosperm tissues, and both can be used as organelles for the accumulation of exogenous peptides. The transport and accumulation of exogenous peptides in PB-IIs has so far been proved in kidney bean seed storage protein β phaseolin (Zheng, Z., Sumi, K., Tanaka, K., and Murai, N. 1995, Plant Physiol. 109, 777-786) and soy bean seed storage protein, glycinin (Katsube, T., Kurisaka, N., Ogawa, M., Maruyama, N., Ohtsuka, R., Utsumi, S., and Takaiwa, F. 1999, Plant Physiol. 120, 1063-1073). On the other hand, there is no proven example of the transport and accumulation of exogenous peptides to PB-Is. Thus, the present invention addresses this deficiency by enabling transport and accumulation of exogenous peptides in PB-Is. In addition, prolamine-accumulating PB-Is are known to have extremely bad digestibility in humans and animals (Tanaka, Y., Hayashida, S., and Hongo, M. 1975, Agric. Biol. Chem. 39, 515-518). This phenomenon is presumed to closely relate to crystallization due to intermolecular interactions between prolamine proteins. Thus, exogenous peptide transport to and accumulating in PB-Is allows for the prevention of interactions between prolamines, thereby resulting in a change in the properties of PB-Is. Potential benefits of changing the properties of PB-Is include improving nutritional characteristics by increased prolamine digestibility, and altering cooking behavior and processing characteristics.

The invention claimed is:

1. A method for accumulating an arbitrary peptide in a type I protein body in the endosperm tissue of a plant, which comprises the steps of:

(a) introducing into a plant cell a vector comprising a DNA encoding a fusion peptide arising by fusing an arbitrary peptide with a peptide comprising at least the amino acid sequence of SEQ ID NO:5 and having the activity of accumulating in a type I protein body in a plant endosperm tissue;

(b) expressing said DNA in the plant cell;

(c) regenerating the plant cell into a plant; and (d) accumulating the fusion peptide in a type I protein body in the endosperm tissue of the plant of step (c).

2. The method of claim 1, wherein the plant is a gramineous plant or a rice plant.

* * * * *

SEQUENCE LISTING

<160> NUMBER OF SEQ ID NOS: 18

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Consensus
      Sequence
<220> FEATURE:
<221> NAME/KEY: SITE
<222> LOCATION: (4)
<223> OTHER INFORMATION: Xaa = any amino acid

<400> SEQUENCE: 1

Gln Cys Cys Xaa Gln
 1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Consensus
      Sequence
<220> FEATURE:
<221> NAME/KEY: SITE
<222> LOCATION: (4)
<223> OTHER INFORMATION: Xaa = Gln, Met, or Arg

<400> SEQUENCE: 2

Gln Cys Cys Xaa Gln
 1               5

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Consensus
      Sequence
<220> FEATURE:
<221> NAME/KEY: SITE
<222> LOCATION: (1)
<223> OTHER INFORMATION: Xaa = Leu or Met
<220> FEATURE:
<221> NAME/KEY: SITE
<222> LOCATION: (2)
<223> OTHER INFORMATION: Xaa = Arg or Gln
<220> FEATURE:
<221> NAME/KEY: SITE
<222> LOCATION: (3)
<223> OTHER INFORMATION: Xaa = Met, Gln, or Arg
<220> FEATURE:
<221> NAME/KEY: SITE
<222> LOCATION: (7)
<223> OTHER INFORMATION: Xaa = Gln, Met, or Arg
<220> FEATURE:
<221> NAME/KEY: SITE
<222> LOCATION: (9)
<223> OTHER INFORMATION: Xaa = Leu, Met, or Gln
<220> FEATURE:
<221> NAME/KEY: SITE
<222> LOCATION: (10)
<223> OTHER INFORMATION: Xaa = Gln, Arg, Met, or Ala
<220> FEATURE:
<221> NAME/KEY: SITE
<222> LOCATION: (11)
<223> OTHER INFORMATION: Xaa = any amino acid
<220> FEATURE:
<221> NAME/KEY: SITE
<222> LOCATION: (12)

<223> OTHER INFORMATION: Xaa = Val, Met, or Ile

<400> SEQUENCE: 3

Xaa Xaa Xaa Gln Cys Cys Xaa Gln Xaa Xaa Xaa
1               5                   10

<210> SEQ ID NO 4
<211> LENGTH: 12
<212> TYPE: PRT
<213> ORGANISM: Oryza sativa

<400> SEQUENCE: 4

Leu Arg Met Gln Cys Cys Gln Gln Leu Gln Asp Val
1               5                   10

<210> SEQ ID NO 5
<211> LENGTH: 15
<212> TYPE: PRT
<213> ORGANISM: Oryza sativa

<400> SEQUENCE: 5

Leu Gly Leu Arg Met Gln Cys Cys Gln Gln Leu Gln Asp Val Ser
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: An
      Artificially Synthesized Peptide Sequence

<400> SEQUENCE: 6

Leu Gly Leu Ala Met Gln Ala Ala Gln Gln Ala Gln Asp Val Ser
1               5                   10                  15

<210> SEQ ID NO 7
<211> LENGTH: 91
<212> TYPE: PRT
<213> ORGANISM: Oryza sativa

<400> SEQUENCE: 7

Gly Ala Gln Val Ser Glu Ser Glu Met Arg Phe Arg Asp Arg Gln Cys
1               5                   10                  15

Gln Arg Glu Val Gln Asp Ser Pro Leu Asp Ala Cys Arg Gln Val Leu
            20                  25                  30

Asp Arg Gln Leu Thr Gly Arg Glu Arg Phe Gln Pro Met Phe Arg Arg
        35                  40                  45

Pro Gly Ala Leu Gly Leu Arg Met Gln Cys Cys Gln Gln Leu Gln Asp
    50                  55                  60

Val Ser Arg Glu Cys Arg Cys Ala Ala Ile Arg Arg Met Val Arg Ser
65                  70                  75                  80

Tyr Glu Glu Ser Met Pro Met Pro Leu Glu Gln
                85                  90

<210> SEQ ID NO 8
<211> LENGTH: 15
<212> TYPE: PRT
<213> ORGANISM: Oryza sativa

<400> SEQUENCE: 8

Gln Val Met Arg Gln Gln Cys Cys Gln Gln Met Arg Leu Met Ala
1               5                   10                  15

```
<210> SEQ ID NO 9
<211> LENGTH: 15
<212> TYPE: PRT
<213> ORGANISM: Oryza sativa

<400> SEQUENCE: 9

Gln Val Met Gln Gln Gln Cys Cys Gln Gln Leu Arg Met Ile Ala
 1               5                  10                  15

<210> SEQ ID NO 10
<211> LENGTH: 15
<212> TYPE: PRT
<213> ORGANISM: Oryza sativa

<400> SEQUENCE: 10

Gln Val Met Gln Gln Gln Cys Cys Gln Gln Leu Arg Leu Val Ala
 1               5                  10                  15

<210> SEQ ID NO 11
<211> LENGTH: 15
<212> TYPE: PRT
<213> ORGANISM: Oryza sativa

<400> SEQUENCE: 11

Ala Leu Leu Gln Gln Gln Cys Cys Met Gln Leu Gln Gly Met Met
 1               5                  10                  15

<210> SEQ ID NO 12
<211> LENGTH: 15
<212> TYPE: PRT
<213> ORGANISM: Zea mays

<400> SEQUENCE: 12

Gln Pro Leu Arg Gln Gln Cys Cys Gln Gln Met Arg Met Met
 1               5                  10                  15

<210> SEQ ID NO 13
<211> LENGTH: 15
<212> TYPE: PRT
<213> ORGANISM: Avena sativa

<400> SEQUENCE: 13

His Val Met Arg Arg Gln Cys Cys Arg Gln Leu Ala Gln Ile Pro
 1               5                  10                  15

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Consensus
      Sequence

<400> SEQUENCE: 14

Gln Cys Cys Gln Gln
 1               5

<210> SEQ ID NO 15
<211> LENGTH: 5
<212> TYPE: PRT
<213> ORGANISM: Oryza sativa

<400> SEQUENCE: 15

Gln Cys Cys Met Gln
```

```
-continued 1               5

<210> SEQ ID NO 16
<211> LENGTH: 5
<212> TYPE: PRT
<213> ORGANISM: Avena sativa

<400> SEQUENCE: 16

Gln Cys Cys Arg Gln
  1               5

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: An
      Artificially Synthesized Peptide Sequence

<400> SEQUENCE: 17

Lys Asp Glu Leu
  1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: An
      Artificially Synthesized Peptide Sequence

<400> SEQUENCE: 18

His Asp Glu Leu
  1
```